(12) United States Patent
O'Lenick

(10) Patent No.: US 8,465,730 B1
(45) Date of Patent: Jun. 18, 2013

(54) POLYGLYCEROL POLYESTERS

(75) Inventor: Thomas G. O'Lenick, Dacula, GA (US)

(73) Assignee: SurfaTech Corporation, Lawrenceville, GA (US)

( * ) Notice: Subject to any disclaimer, the term of this patent is extended or adjusted under 35 U.S.C. 154(b) by 0 days.

(21) Appl. No.: 13/506,163

(22) Filed: Apr. 2, 2012

Related U.S. Application Data

(60) Provisional application No. 61/633,102, filed on Feb. 6, 2012.

(51) Int. Cl.
*A61K 8/00* (2006.01)
*A61K 8/72* (2006.01)

(52) U.S. Cl.
USPC .......................................... 424/59; 424/70.11

(58) Field of Classification Search
None
See application file for complete search history.

(56) References Cited

U.S. PATENT DOCUMENTS 6,280,709 B1 * 8/2001 Papadakos ...................... 424/59
7,638,116 B2 * 12/2009 LaVay et al. ............... 424/70.11

* cited by examiner

*Primary Examiner* — Ernst Arnold
*Assistant Examiner* — Jianfeng Song

(57) ABSTRACT

The present invention is directed toward a series of polyesters with tunable ascetics and skin conditioning properties for use in cosmetic formulation, specifically sun screening formulations in which the performance is improved by a synergistic effect between the sunscreening actives and the polyester. These novel polyglycerol polyesters are designed to be multidimensional. The physical properties and aesthetics of the current invention can be tuned rapidly by controlling the ratio of fatty groups, as well as the cross-linker used. The resulting polyglycerol polyesters have outstanding aesthetics and physical properties.

18 Claims, No Drawings

POLYGLYCEROL POLYESTERS

RELATED APPLICATIONS

This application claims priority to and benefit of U.S. Provisional Application No. 61/633,102 filed Feb. 6, 2012, the disclosure of which is incorporated herein for all purposes.

FIELD OF THE INVENTION

The present invention is directed toward a series of polyglycerol polyesters with tunable ascetics and performance in cosmetic formulation. These novel polyglycerol polyesters are designed to be multidimensional. Multidimensional is meant that the polymer contains a variety of groups containing different chemical and physical properties covalently bonded together. The physical properties of the current invention can be tuned rapidly by controlling the ratio of fatty groups, as well as the cross-linker used. Tuned here is meant the ability to adjust the physical properties to a desired value. The resulting polyglycerol polyesters have outstanding aesthetics and physical properties.

BACKGROUND OF THE INVENTION

Polyglycerol compounds are well known materials. They are made by the condensation reaction of glycerin. The resulting products are polar and posses several un-reacted hydroxyl groups. The number of glycerin molecules condensed in the reaction is referred to as the degree of polymerization (DP). The condensation reaction run between two glycerin molecules produces water as a byproduct. U.S. Pat. No. 5,721,305 issued Feb. 24, 1998 to Eshuis, et al. entitled Polyglycerol production teaches how polyglycerol is made.

U.S. Pat. No. 3,936,391 issued Feb. 3, 1976 to Gabby entitled "Hydrated polyglycerol Ester Composition" teaches a polyglycerol ester emulsifier is prepared by heating a polyglycerol ester containing 3 to 10 glycerol units and a 1 to 2 saturated fatty acyl ester groups containing 16 to 20 carbon atoms, glycerol and water at a temperature of 125 to 135° F. The heat is maintained until a homogeneous paste-like consistency is imparted thereto.

U.S. Pat. No. 5,674,475 issued Oct. 7, 1997 to Dahms entitled "Emulsifier Composition based on Polyglycerol Ester" teaches an emulsifier composition of a mixture of polyglycerol fatty acid esters and the lactylate of a fatty acid or its salt. This emulsifier is used to manufacture a wide range of different oil in water emulsions.

U.S. Pat. No. 1,424,137 issued July 1922 to Weisberg, entitled "Polyglycerol Resins" discloses a polyglycerol ester of an aromatic dibasic acid used in shellac. This patent, imported herein by reference, addresses solid resins made in solvent. While lacking the critical control of cross-linking and producing a hard rather than a soft ester, this patent shows the state of the art in resins.

Still another U.S. Pat. No. 7,638,116, issued Dec. 29, 2009 by LaVay et al. entitled "Polyglycerol dimer polyester resins" discloses a polyglycerol dimer resin of a polyglycerol containing 3 to 10 repeat units cross-linked by dimer acid. While lacking the critical control of cross-linking and functionalization by fatty groups, this patent shows the state of the art of polyglycerol dimer polyesters.

UVA protection has been a source of increasing discussion worldwide due to the steadily climbing rates of skin cancer, and particularly malignant melanoma. There have been many who say one of the problems has been the emphasis on SPF, which have steadily increased, and not enough emphasis on UVA protection. The SPF test is a measurement of erythema and 85% to 90% of the erytema energy is UVB energy. While this means that to obtain SPFs higher than 10, some UVA protection must be present the SPF test provides little indication of the magnitude of the UVA protection. In fact, based on the 2007 FDA Sunscreen Monograph, Sunscreen Drug Products for Over-the-Counter Human Use; Proposed Amendment of Final Monograph; Proposed Rule, (2007 Monograph) the instruments utilized to test SPF may have as little as 9% of the erythemal energy coming from UVA and as little as 3% of the erythemal energy coming from UVAI energy. UVA energy is defined as the Ultraviolet energy from 320 nm to 400 nm and UVAI energy is defined as energy from 340 nm to 400 nm. There are several UVA tests that exist worldwide, but only since the 2007 Monograph has there been anything official in the US. The 2007 monograph lists two UVA tests that must be performed. One test, the JCIA Persistent Pigment Darkening test compares the amount of energy needed to produce melagenesis(tan) in unprotected skin versus the amount of energy needed to produce a tan in protected skin. This test predominantly is based on the amount of UV energy absorbed in the UVAII, 320 nm to 340 nm area of the Ultraviolet spectra. The FDA recognizing this devised a second test to measure the energy absorbed in the UVAI area of the spectra. Simply stated, this in vitro test is based on dividing the average amount of absorbance in the UVAI area by the average amount of absorbance in the entire UV spectra.

The resultant ratio determines the amount of UVA protection that can be labeled. Front panel labeling is required to reflect this by a star system and descriptor system as follows:

| UVAI/UV Ratio | Descriptor | No. of Stars |
| --- | --- | --- |
| <20 | No UVA claim | 0 |
| .20-.39 | Low UVA | 1 |
| .40-.69 | Medium | 2 |
| .70-.95 | High | 3 |
| >0.95 | Highest | 4 |

To obtain the desired ratio, product absorbance must have increasing magnitude of absorbance in the UVA region and increasing breadth in the longer UVAI wavelengths. To obtain the highest rating the product needs to absorb as much in the long UVAI wavelengths as is absorbed in the shorter wavelengths. While this sounds simple in theory, it is very contradictory to common sunscreen products in the US as well as the world, which almost always have the predominant amount of their absorbance in the UVB region and then rapidly taper off in the UVAII and UVAI. Obtaining the highest ratio with an SPF of 30 or higher is practically impossible with existing US approved sunscreen active materials without using a product so opaque that few if any would use.

The only chemical sunscreen available to use in the US that absorbs with any significance in the UVAI region is Butyl Methoxydibenzoylmethane, more commonly known as Avobenzone. And even Avobenzone is woefully lacking in producing the broad coverage needed to obtain a 4 star, high SPF product since the maximum absorbance of Avobenzone in a polar solvent such as ethanol is 357 nm and the absorbance drops off extremely fast at increasingly higher wavelengths. The maximum absorbance is even lower in non-polar solvents such as most oils. This situation is exacerbated by the fact that once an alcohol product is applied to the skin the alcohol quickly evaporates leaving the Avobenzone in an increasingly polar environment. Further to that most sunscreen products are in fact emulsions that have the Avobenzone dissolved in a non-polar oil phase in order for it to be solubilized and emulsified. The maximum absorbance in some commonly used oil ingredients used to solubilize and emulsify Avobenzone have in fact much lower maximum absorptions. For example Avobenzone maximum absorbance in Mineral Oil is only at at 351 nm and C12-15 Alkyls Benzoate is at 355 nm. Note a typical absorption pattern for Avobenzone in C12-15 alkyl benzoate, run using a UV-Visible spectrophotometer results in a spectrum with very little absobance in the range of 390 nm. Improving the absorbance at this wavelength would result in an improved star rating.

It is known in the art that light radiation of wavelengths of from 290 to 320 nm, i.e., UV-B irradiation, causes skin burning and erythema. For these reasons, as well as for aesthetic reasons, there is an increasing demand for means of controlling this natural tanning in order to thereby control the color of the skin. This UV-B radiation must thus be screened from the skin."

It is also known to this art that UV-A radiation, of wavelengths of from 320 to 400 nm, which tan the skin, also adversely affects it, especially in the case of sensitive skin or skin which is continually exposed to solar radiation. UV-A rays especially cause a loss in the elasticity of the skin and the appearance of wrinkles, promoting premature skin aging. Such irradiation promotes triggering of the erythemal reaction or amplifies this reaction in certain individuals and may even be the source of phototoxic or photoallergic reactions. Thus, for aesthetic and cosmetic reasons, such as conservation of the natural elasticity of the skin, for example, an ever-increasing number of individuals wish to control the effect of UV-A rays on their skin, it is desirable to also screen out UV-A radiation.

A wide variety of compounds suited for photoprotection (UV-A and/or UV-B) of the skin are known to this art. Most of these are aromatic compounds exhibiting absorption of UV radiation in the region from 280 to 315 nm, or in the region from 315 to 400 nm, or in both of these regions. There is no good way known at present to modify the absorption properties of molecules to meet the specific needs, or to combine products to cover a wide range of UV wavelengths. Products heretofore known are typically formulated into antisun or sunscreen compositions which are in the form of an emulsion of oil-in-water type or water in oil type, and which thus contain, in various concentrations, one or more conventional lipophilic and/or hydrophilic organic screening agents. These are capable of selectively absorbing harmful UV radiation of specific wavelength, depending upon structure of such screening agents (and their amounts) being selected as a function of the desired sun protection factor SPF (the sun protection factor being expressed mathematically by the ratio of the irradiation time required to attain the erythema-forming threshold with the UV screening agent to the time required to attain the erythema-forming threshold in the absence of UV screening agent).

It is a long felt need to have a sunscreening agent that can absorb ultra violet radiation at specific desired wavelengths. In addition, these compounds exhibiting anti-UV activity must also have good cosmetic properties in compositions comprised thereof, good solubility in the usual solvents, and in particular fatty substances such as oils and greases, as well as good resistance to water and to perspiration.

None of the references above understood the desirability of incorporation of fatty groups incorporated onto a polyglycerol backbone to produce an unknown polymer that acts synergistically to improve sunscreening performance.

The Invention

Object of the Invention

The current invention is directed toward a series of multi-domain polyglycerol polyesters that are synthesized by the reaction of polyglycerol, a diacid and a mixture of fatty acids. These multidimensional polyglycerol polyesters contain a mixture of fatty groups with differing melt points. The multi-domain nature of the current invention will provide very unique physical properties and ascetics in cosmetic formulations.

Another aspect of the present invention is a process for providing improved sun protection to the skin, which comprises contacting the skin with an effective sun protection concentration of a composition which comprises:

(a) a polyester conforming to the following structure:

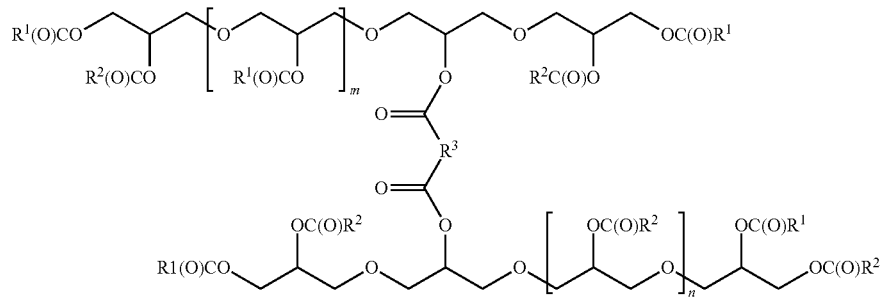

wherein, $R^1$ is an alkyl containing 8 to 26 carbons, or mixtures thereof;

$R^2$ is an alkyl containing 8 to 26 carbons or mixtures thereof;

$R^3$ is independently selected from an alkyl containing 2 to 12 carbons, or an alkyl confining to the following structure:

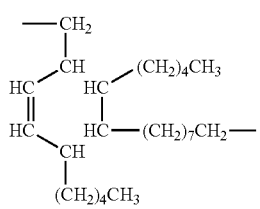

or

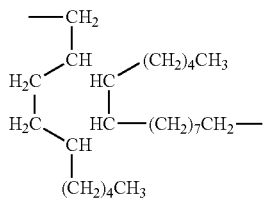

or mixtures thereof;
n is an integer ranging from 0 to 9;
m is an integer ranging from 0 to 9
and
a sunscreening active.

The effective conditioning concentration ranges from 5.0% and 55.0% by weight sunscreening actives and 5% to 25% by weight polyester Sunscreening active is defined herein below.

SUMMARY OF THE INVENTION

The present invention is related to a series of novel polyglycerol polyesters that are prepared by the reaction of a mixture of fatty acids, polyglycerol and a diacid. The nature of a polymer that contains different physical properties mainly the difference between the water loving nature of polyglycerol and the physical properties of the fatty group produces products that have extremely unique properties. The selection of the fatty groups, the diacid, and polyglycerol will drastically change the physical and cosmetic aesthetics of the resulting material.

The compounds of the present invention are made by the esterification reaction of a diacid, polyglycerol, and a mixture of at least two fatty acids. The resulting products have the compatibility over those materials lacking the combination of these groups. This combination of groups results in a high efficient deposition of the skin, hair and fibers.

DETAILED DESCRIPTION OF THE INVENTION

The present invention is aimed at a series of novel multi-domain polyglycerol polyester that provides desired aesthetics and structure in cosmetic formulations.

Polyglycerol Polyester

A polyester conforming to the following structure:

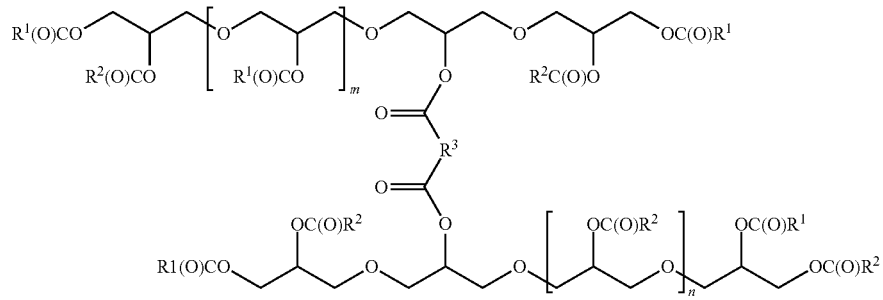

wherein,
$R^1$ is an alkyl containing 8 to 26 carbons, or mixtures thereof;
$R^2$ is an alkyl containing 8 to 26 carbons or mixtures thereof;
$R^3$ is independently selected from an alkyl containing 2 to 12 carbons, or an alkyl confining to the following structure:

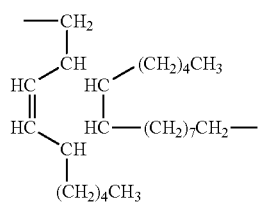

or

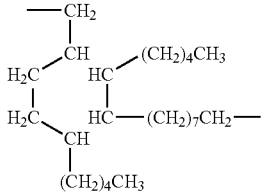

or mixtures thereof;
n is an integer ranging from 0 to 9;
m is an integer ranging from 0 to 9.

Another aspect of the present invention is a process for providing improved sun protection to the skin, which comprises contacting the skin with an effective sun protection concentration of a composition which comprises:
(a) a polyester conforming to the following structure:

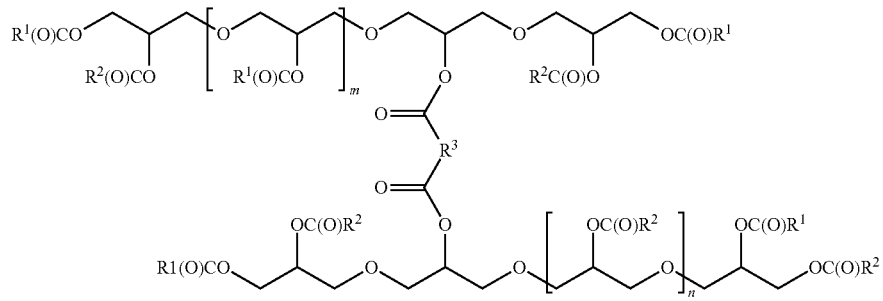

wherein,
$R^1$ is an alkyl containing 8 to 26 carbons, or mixtures thereof;
$R^2$ is an alkyl containing 8 to 26 carbons or mixtures thereof;
$R^3$ is independently selected from an alkyl containing 2 to 12 carbons, or an alkyl confining to the following structure:

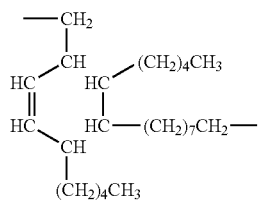

or

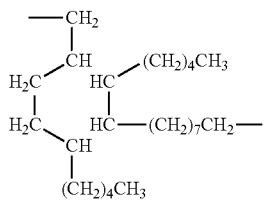

or mixtures thereof;
n is an integer ranging from 0 to 9;
m is an integer ranging from 0 to 9
and
a sunscreening active.

The effective conditioning concentration ranges from 5.0% and 55.0% by weight sunscreening actives and 5% to 25% by weight polyester Sunscreening active is defined herein below.

Preferred Embodiment

In a preferred embodiment $R^1$ and $R^2$ are different.
In a more preferred embodiment one of $R^1$ and $R^2$ is solid and the other is liquid, (as used herein, liquid is meant pourable at 25° C., by solid is meant solid at 25° C.).
In a more preferred embodiment $R^1$ is an alkyl having 18 carbons.
In a more preferred embodiment $R^3$ is dimer acid.

In a more preferred embodiment $R^2$ is an alkyl having 18 carbons.
In a more preferred embodiment $R^3$ is an alkyl having 7 carbons.
In a more preferred embodiment n is 0;
In a more preferred embodiment m is 0;

Raw Materials

Fatty Acids

Fatty acids useful in the practice of the present invention are items of commerce commercially available from Cognis.

Fatty Acid Names

Fatty acids useful as raw materials in the preparation of compounds of the present invention are commercially available from a variety of sources including Procter and Gamble of Cincinnati Ohio. The structures are well known to those skilled in the art.

$$R-C(O)-OH$$

| Saturated | | | |
|---|---|---|---|
| Example | R Formula | Common Name | Molecular Weight |
| 1 | $C_7H_5$ | Caprylic | 144 |
| 2 | $C_9H_{19}$ | Capric | 172 |
| 3 | $C_{11}H_{23}$ | Lauric | 200 |
| 4 | $C_{13}H_{27}$ | Myristic | 228 |
| 5 | $C_{14}H_{29}$ | Pentadecanoic | 242 |
| 6 | $C_{15}H_{31}$ | Palmitic | 256 |
| 7 | $C_{17}H_{35}$ | Stearic | 284 |
| 8 | $C_{17}H_{35}$ | Isosteric | 284 |
| 9 | $C_{19}H_{39}$ | Arachidinic | 312 |
| 10 | $C_{21}H_{43}$ | Behenic | 340 |
| 12 | $C_{26}H_{53}$ | cetrotic | 396 |
| 13 | $C_{33}H_{67}$ | geddic acid | 508 |

| Unsaturated | | | |
|---|---|---|---|
| Example | R Formula | Common Name | Molecular Weight |
| 14 | $C_{17}H_{33}$ | Oleic | 282 |
| 15 | $C_{17}H_{31}$ | Linoleic | 280 |
| 16 | $C_{17}H_{29}$ | Linolenic | 278 |
| 17 | $C_{15}H_{29}$ | Palmitoleic | 254 |
| 18 | $C_{13}H_{25}$ | Myristicoleic | 226 |
| 19 | $C_{21}H_{41}$ | Erucic | 338 |

Polyglycerol

Polyglycerol is useful as raw materials in the preparation of compounds of the present invention. Polyglycerols are commercially available from a variety of sources including Solvay Chemicals of Rheinberg Germany.

The structures are well known to those skilled in the art.

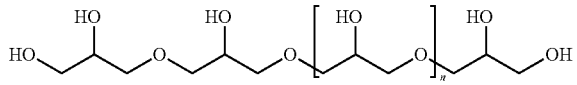

wherein;
n is an integer ranging from 0 to 9.

| Example | n | MW |
|---------|---|-------|
| 20 | 0 | 225.0 |
| 21 | 3 | 450.0 |
| 22 | 7 | 750.0 |

Example 23

Dimer Acid

Dimer acid is an item of commerce available commercially from Cognis Corporation. It conforms to the following structure:

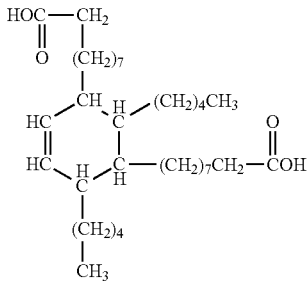

Example 24

Hydrogenated Dimer Acid

Hydrogenated dimer acid is an item of commerce available commercially from Henkel Corporation. It conforms to the following structure:

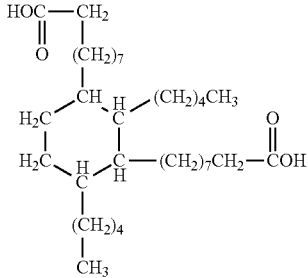

Dicarboxylic Acid

Dicarboxylic acid useful as raw materials in the synthesis of the compounds of the present invention are commercially available from a variety of sources including Cognis. They conform to the following structure;

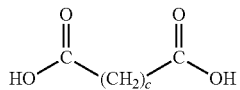

wherein;
c is an integer ranging from 1 to 10.

| Saturated Dicarboxylic acids | | | |
|---------|-------------|----|------------------|
| Example | Common Name | c | Molecular Weight |
| 25 | Malonic | 1 | 104 |
| 26 | Succinic | 2 | 118 |
| 27 | Glutaric | 3 | 132 |
| 28 | Adipic | 4 | 146 |
| 29 | Pimelic | 5 | 160 |
| 30 | Subric | 6 | 174 |
| 31 | Azelaic | 7 | 188 |
| 32 | Sebacic | 8 | 202 |
| 33 | Undecanedioic | 9 | 216 |
| 34 | Dodecanedioic | 10 | 230 |

General Procedure

A specified number of grams polyglycerol (examples 20-22) is added to a specified amount of fatty acids (examples 1-18) and a diacid (examples 23 and 34). The reaction mixture is heated to 160-180° C. Water is removed by vacuum during the reaction process. The reaction is monitored by the determination of acid value. The acid value will diminish as the reaction proceeds. The reaction is cooled once the acid value fails to change over an additional two hours at elevated temperature. The product is used without purification.

| | Polyglycerol | | $R^1$ | | $R^2$ | | Diacid | |
|---------|---------|-------|---------|-------|---------|-------|---------|-------|
| Example | Example | Grams | Example | Grams | Example | Grams | Example | Grams |
| 35 | 20 | 33.8 | 8 | 85.5 | 7 | 85.5 | 24 | 45.1 |
| 36 | 20 | 33.8 | 8 | 149.7 | 7 | 21.4 | 23 | 45.1 |
| 37 | 20 | 31.8 | 14 | 79.7 | 10 | 96.0 | 24 | 42.5 |
| 38 | 20 | 33.4 | 14 | 146.6 | 10 | 25.3 | 24 | 44.7 |
| 39 | 20 | 31.7 | 8 | 80.2 | 10 | 95.8 | 23 | 42.3 |
| 40 | 20 | 33.3 | 8 | 147.2 | 10 | 25.1 | 23 | 44.4 |
| 41 | 20 | 33.9 | 14 | 85.0 | 7 | 85.7 | 24 | 45.4 |
| 42 | 20 | 34.0 | 14 | 149.1 | 7 | 45.1 | 24 | 45.5 |
| 43 | 21 | 85.7 | 8 | 65.0 | 7 | 65.0 | 23 | 34.3 |
| 44 | 21 | 85.7 | 8 | 113.8 | 7 | 16.3 | 23 | 34.3 |
| 45 | 21 | 81.7 | 14 | 61.4 | 10 | 74.1 | 24 | 32.8 |
| 46 | 21 | 84.9 | 14 | 111.8 | 10 | 19.2 | 24 | 34.1 |
| 47 | 21 | 81.6 | 8 | 61.9 | 10 | 73.9 | 23 | 32.6 |
| 48 | 21 | 84.6 | 8 | 112.3 | 10 | 19.2 | 23 | 33.8 |
| 49 | 21 | 85.9 | 14 | 64.6 | 7 | 65.1 | 24 | 34.5 |
| 50 | 21 | 86.0 | 14 | 113.2 | 7 | 16.3 | 24 | 34.3 |
| 51 | 22 | 59.6 | 8 | 75.3 | 7 | 75.3 | 23 | 39.7 |
| 52 | 22 | 59.6 | 8 | 131.9 | 7 | 18.8 | 23 | 39.7 |
| 53 | 22 | 56.4 | 14 | 70.7 | 10 | 85.2 | 24 | 37.7 |
| 54 | 22 | 59.0 | 14 | 129.3 | 10 | 22.3 | 24 | 39.4 |
| 55 | 22 | 56.3 | 8 | 71.2 | 10 | 85.0 | 23 | 37.5 |
| 56 | 22 | 58.7 | 8 | 129.9 | 10 | 22.2 | 23 | 39.1 |
| 57 | 22 | 59.7 | 14 | 74.8 | 7 | 75.5 | 24 | 39.9 |
| 58 | 22 | 59.8 | 14 | 131.2 | 7 | 18.9 | 24 | 40.0 |
| 59 | 20 | 39.6 | 8 | 100.0 | 7 | 100.0 | 26 | 10.4 |
| 60 | 20 | 39.6 | 8 | 175.1 | 7 | 25.0 | 26 | 10.4 |
| 61 | 21 | 89.8 | 14 | 67.5 | 10 | 81.4 | 31 | 11.3 |
| 62 | 21 | 93.7 | 14 | 123.3 | 10 | 21.2 | 31 | 11.7 |

-continued

| | Polyglycerol | | R¹ | | R² | | Diacid | |
|---|---|---|---|---|---|---|---|---|
| Example | Example | Grams | Example | Grams | Example | Grams | Example | Grams |
| 63 | 22 | 62.5 | 8 | 79.0 | 10 | 94.4 | 32 | 14.0 |
| 64 | 22 | 65.5 | 8 | 145.0 | 10 | 24.8 | 32 | 14.7 |
| 65 | 20 | 38.2 | 14 | 95.7 | 7 | 96.6 | 34 | 19.5 |
| 66 | 20 | 34.0 | 14 | 149.1 | 7 | 21.5 | 34 | 45.5 |
| 67 | 20 | 33.9 | 8 | 85.8 | 14 | 85.0 | 23 | 45.2 |
| 68 | 20 | 38.8 | 14 | 170.4 | 7 | 24.6 | 31 | 16.2 |

Applications

The compounds of the present invention when added to alcoholic solutions, surprisingly and unexpectedly produce outstanding film formation and provide outstanding aesthetics to cosmetic formulations. Furthermore, the compounds of the present invention when added into a sunscreen or sunblock formulation, surprisingly and unexpectedly produce waterproofing on the skin.

Several sunscreen formulations were prepared using polyglycerol polyesters and the absorbance and improvement in sun protection factor was monitored. The formulations were prepared by heating the organic filters and polyglycerol polyesters in C12 15 alkyl benzoate. Alcohol was then added into this solution and stirred until a homogeneous solution was obtained. A detailed breakdown of the formulation is shown below.

Sun Screening Agents

Avobenzone

The only chemical sunscreen available to use in the US that absorbs with any significance in the UVAI region is Butyl Methoxydibenzoylmethane, more commonly known as Avobenzone. And even Avobenzone is woefully lacking in producing the broad coverage needed to obtain a 4 star, high SPF product since the maximum absorbance of Avobenzone in a polar solvent such as ethanol is 357 nm and the absorbance drops off extremely fast at increasingly higher wavelengths. The maximum absorbance is even lower in non-polar solvents such as most oils. This situation is exacerbated by the fact that once an alcohol product is applied to the skin the alcohol quickly evaporates leaving the Avobenzone in an increasingly polar environment. Further to that most sunscreen products are in fact emulsions that have the Avobenzone dissolved in a non-polar oil phase in order for it to be solubilized and emulsified. Avobenzone is useful in the compositions at a range of between 1 to 3% by weight.

Organic sunscreens known to those of skill in the art are suitable for use in combination with the SPF enhancing polymer of the present invention. In aspects of the present invention directed to personal care products intended for contact with human skin, approval by a regulatory agency is required. Accordingly, organic sunscreen active agents suitable for use with the SPF enhancing polymer of the present invention include those which are currently approved by the US Food and Drug Administration in the Sunscreen Drug Products for Over-The-Counter Human Use Final Monograph as published in the Federal Register on May 21, 1999 at Volume 64, Number 98, pages 27666-27693. Organic sunscreens currently approved by the FDA are as follows, (referred herein as sunscreening actives): p-Aminobenzoic acid (PABA) up to 15%; Avobenzone up to 3%; Cinoxate up to 3%; Dioxybenzone up to 3%; Homosalate up to 15%; Menthyl anthranilate up to 5%; Octocrylene up to 10%; Octyl methoxycinnamate (Octinoxate) up to 7.5%; Octyl salicylate up to 5%; Oxybenzone up to 6%; Padimate 0 up to 8%; Phenylbenzimidazole sulfonic acid (Ensulizole) up to 4%; Sulisobenzone up to 10%; Trolamine salicylate up to 12%.

Other sunscreening actives as referred to herein include ingredients accepted for use in products intended to contact human skin that are approved in countries outside the US are also considered to be within the scope of the present invention. Other examples of organic sunscreening actives (as used herein) include not currently approved by the FDA but suitable for use in combination with the SPF-enhancing polymer of Formula I include the following: 4-Methylbenzylidene camphor (USAN Enzacamene); Methylene Bis-Benzotriazolyl Tetramethylbutylphenol (USAN Bisoctrizole) marketed under the tradename Tinosorb® M; Bis-Ethylhexyloxyphenol Methoxyphenyl Triazine (USAN Bemotrizinol) marketed under the tradename marketed under the tradename Tinosorb® S; Terephthalylidene Dicamphor Sulfonic Acid (USAN Ecamsule) marketed under the tradename Mexoryl® SX; Drometrizole Trisiloxane marketed under the tradename Mexoryl® XL; Disodium Phenyl Dibenzimidazole Tetrasulfonate marketed under the tradename Neo Heliopan® AP; Diethylamino Hydroxybenzoyl Hexyl Benzoate marketed under the tradename Uvinul® A Plus; Octyl Triazone marketed under the tradename Uvinul® T 150; Diethylhexyl Butamido Triazone marketed under the tradename Uvasorb® HEB; Polysilicone-15 marketed under the tradename Parsol® SLX.

Sunscreening Formulations

Compounds of U.S. Pat. No. 7,638,116

| | Concentration (wt %) Formulation | |
|---|---|---|
| Material | D | E |
| Avobenzone | 3.0 | 3.0 |
| Homosalate | 8.7 | 8.7 |
| Octinoxate | 5.0 | 5.0 |
| Octisalate | 5.0 | 5.0 |
| Octocrylene | 2.5 | 2.5 |
| Oxybenzone | 5.0 | 5.0 |
| SD Alcohol | 50.0 | 50.0 |
| C12 15 Alkyl Benzoate | 15.5 | 15.5 |
| Cyclomethicone (D5) (control) | 5.0 | 0.0 |
| 7,638,116 Example 13 | 5.0 | 0.0 |
| 7,638,116 Example 17 | 0.0 | 5.0 |

Present Invention

| Formulation | Critical Wavelength (nm) | Increase in SPF (in vitro) (%) | SPF (in vivo) (%) |
|---|---|---|---|
| A | 377.3 | 0.0 | 35 |
| B | 376.8 | 19.5 | 42 |
| C | 376.5 | 10.4 | 39 |

Examples 35 and examples 68 of the current invention show an increase in SPF (in vitro) of 19.5 and 10.4 respectively. This results shows that these materials can be used in sunscreen formulations, specifically alcoholic sunscreen formulations, provides an unexpected SPF boost. This boost in SPF provides a more efficient sunscreen formulation. Efficient here is meant a higher SPF value without increasing the amount of sunscreen filters.

U.S. Pat. No. 7,638,116

| Formulation | Critical Wavelength (nm) | Increase in SPF (in vitro) (%) | SPF (in vivo) (%) |
|---|---|---|---|
| D | 377.4 | 0.0 | 34 |
| E | 376.8 | 0.0 | 35 |

The compounds of the LaVay art failed to improve the SPF values. Not wanting to be bound by a specific theory, the LaVay compounds lack any fatty groups on the polymer, thereby lacking both fatty groups and more critically, the specific groups of the present invention.

While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth herein above but rather that the claims be construed as encompassing all the features of patentable novelty which reside in the present invention, including all features which would be treated as equivalents thereof by those skilled in the art to which the invention pertains.

The invention claimed is:

1. A polyglycerol polyester that conforms to the following structure:

wherein, $R^1$ is an alkyl containing 8 to 26 carbons, or mixtures thereof;

$R^2$ is an alkyl containing 8 to 26 carbons or mixtures thereof;

$R^3$ is independently selected from an alkyl containing 2 to 12 carbons, or an alkyl confining to the following structure:

or mixtures thereof;

n is an integer ranging from 0 to 9;

m is an integer ranging from 0 to 9.

2. The polyglycerol polyester of claim 1 wherein $R^1$ and $R^2$ are different.

3. The polyglycerol polyester of claim 1 wherein $R^1$ and $R^2$ are different and $R^1$ is an alkyl having 18 carbons.

4. The polyglycerol polyester of claim 1 wherein $R^3$ is

5. The polyglycerol polyester of claim 1 wherein $R^2$ is an alkyl having 18 carbons.

6. The polyglycerol polyester of claim 1 wherein $R^3$ is an alkyl having 7 carbons.

7. The polyglycerol polyester of claim 1 wherein n is 0.

8. The polyglycerol polyester of claim 1 wherein m is 0.

9. The polyglycerol polyester of claim 1 wherein $R^1$ is alkyl having 8 carbons and $R^2$ is alkyl containing 18 carbons.

10. A process for providing improved sun protection to the skin, which comprises contacting the skin with an effective sun protection concentration of a composition of the polyglycerol polyester of claim 1 and a sunscreening active.

11. The process of claim 10 wherein the effective conditioning concentration ranges from 5.0% and 55.0% by weight sunscreening actives and 5% to 25% by weight polyester.

12. The process of claim 10 wherein $R^1$ and $R^2$ are different.

13. The process of claim 10 wherein $R^1$ and $R^2$ are different and $R^1$ is an alkyl having 18 carbons.

14. The process of claim 10 wherein $R^3$ is
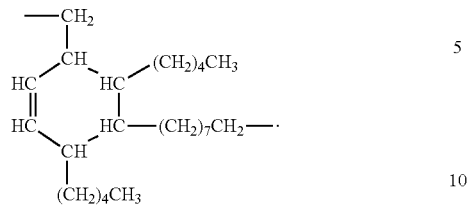
15. The process of claim 10 wherein $R^2$ is an alkyl having 18 carbons.
16. The process of claim 10 wherein $R^3$ is an alkyl having 7 carbons.
17. The process of claim 10 wherein n is 0.
18. The process of claim 10 wherein m is 0.
\* \* \* \* \*